(12) United States Patent
Pacetti et al.

(10) Patent No.: US 9,908,297 B2
(45) Date of Patent: Mar. 6, 2018

(54) SCAFFOLDS HAVING VARIABLE WALL THICKNESS

(71) Applicant: Abbott Cardiovascular Systems Inc., Santa Clara, CA (US)

(72) Inventors: Stephen D. Pacetti, San Jose, CA (US); Chad J. Abunassar, San Francisco, CA (US); Diem U. Ta, San Jose, CA (US); Richard J. Rapoza, San Francisco, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 160 days.

(21) Appl. No.: 14/831,693

(22) Filed: Aug. 20, 2015

(65) Prior Publication Data

US 2017/0049592 A1 Feb. 23, 2017

(51) Int. Cl.
| | | |
|---|---|---|
| *A61F 2/89* | (2013.01) |
| *B29C 69/00* | (2006.01) |
| *A61F 2/915* | (2013.01) |
| *B29C 49/42* | (2006.01) |
| *B29L 31/00* | (2006.01) |
| *A61F 2/91* | (2013.01) |

(52) U.S. Cl.
CPC ............ *B29C 69/001* (2013.01); *A61F 2/915* (2013.01); *B29C 49/4268* (2013.01); *A61F 2/91* (2013.01); *A61F 2002/91575* (2013.01); *A61F 2230/0006* (2013.01); *A61F 2250/0036* (2013.01); *A61F 2250/0098* (2013.01); *B29C 2793/0063* (2013.01); *B29L 2031/7546* (2013.01)

(58) Field of Classification Search
CPC .. A61F 2/915; A61F 2/91; A61F 2002/91575; A61F 2230/0006; A61F 2250/0036; A61F 2250/0098; B29C 69/001; B29C 2793/0063; B29L 2031/7546
USPC .......................................................... 623/1.11
See application file for complete search history.

(56) References Cited

U.S. PATENT DOCUMENTS

| | | | | |
|---|---|---|---|---|
| 4,141,364 | A * | 2/1979 | Schultze ............... | A61M 16/04 128/207.15 |
| 7,740,791 | B2 | 6/2010 | Kleine et al. | |
| 8,002,817 | B2 | 8/2011 | Limon | |
| 8,303,644 | B2 | 11/2012 | Lord et al. | |
| 8,388,673 | B2 | 3/2013 | Yang et al. | |
| 2002/0138133 | A1* | 9/2002 | Lenz .................... | A61F 2/91 623/1.15 |
| 2010/0004735 | A1 | 1/2010 | Yang et al. | |

(Continued)

OTHER PUBLICATIONS

Kolandaivelu et al., "Stent Thrombogenicity Early in High-Risk Interventional Settings Is Driven by Stent Design and Deployment and Protected by Polymer-Drug Coatings", Circulation 123, pp. 1400-1409 (2011).

*Primary Examiner* — Eric Rosen
*Assistant Examiner* — George J Ulsh
(74) *Attorney, Agent, or Firm* — Squire Patton Boggs (US) LLP

(57) ABSTRACT

A scaffold strut is shaped to improve hemocompatibility. The scaffold is made from a tube having variable wall thickness. Methods are disclosed for modifying the thickness of the tube in such a way as to achieve a reduced hemodynamic profile, but without significantly affecting strength properties in areas where stress concentrations exist when the scaffold is loaded.

20 Claims, 13 Drawing Sheets

(56) References Cited

U.S. PATENT DOCUMENTS

| | | | |
|---|---|---|---|
| 2011/0029063 A1* | 2/2011 | Ma | A61F 2/915 |
| | | | 623/1.16 |
| 2011/0066222 A1 | 3/2011 | Wang et al. | |
| 2011/0190872 A1 | 8/2011 | Anukhin et al. | |
| 2012/0035715 A1* | 2/2012 | Robida | A61F 2/848 |
| | | | 623/1.36 |
| 2012/0042501 A1 | 2/2012 | Wang et al. | |
| 2013/0255853 A1 | 10/2013 | Wang et al. | |
| 2015/0018935 A1 | 1/2015 | Pacetti et al. | |

* cited by examiner

SCAFFOLDS HAVING VARIABLE WALL THICKNESS

BACKGROUND OF THE INVENTION

Field of the Invention

The present invention relates to bioresorbable scaffolds; more particularly, this invention relates to bioresorbable scaffolds for treating an anatomical lumen of the body.

Description of the State of the Art

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into the anatomical lumen, advancing the catheter in the anatomical lumen to a desired treatment location, expanding the stent at the treatment location, and removing the catheter from the lumen.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or expanded within a lumen (with or without an assisting balloon). Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris-type or other form of crimper, such as the crimping machine disclosed and illustrated in US 2012/0042501. A significant amount of plastic or inelastic deformation occurs both when the balloon expandable stent or scaffold is crimped and later deployed by a balloon. At the treatment site within the lumen, the stent is expanded by inflating the balloon.

The stent must be able to satisfy a number of basic, functional requirements. The stent (or scaffold) must be capable of sustaining radial compressive forces as it supports walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer needed.

The present application adopts the following definitions of radial strength and radial stiffness. Radial strength, which is the ability of a stent to resist radial compressive forces, relates to a stent's radial yield strength around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force or no incremental force is required to cause major deformation. A radial "stiffness" refers to the amount net radial inward force (i.e., uniform radial inward pressure over the entire abluminal scaffold surface×the abluminal surface area) required to reversibly decrease a scaffold diameter by a certain amount. The slope of the curve from a force-deflection plot will be called the "absolute stiffness" or K. The units are N/mm and the stiffness is expressed for the linearly elastic range of response to the radial force. Thus, for a scaffold deployed to 6.5 mm and having a linear elastic range for radial compression between 6.5 mm and 5.5 mm and a radial stiffness of 20 N/mm, a net inward radial inward force of 10 N is needed to decrease the scaffold diameter from 6.5 mm to 6.0 mm. After the radial force is removed, the scaffold returns to the 6.5 mm diameter.

Scaffolds have been made from a bioresorbable polymer. Examples of bioresorbable polymer scaffolds include those described in U.S. Pat. No. 8,002,817 to Limon, U.S. Pat. No. 8,303,644 to Lord, and U.S. Pat. No. 8,388,673 to Yang. FIG. 1 shows an end segment of a bioresorbable polymer scaffold designed for delivery through anatomical lumen using a catheter and plastically expanded using a balloon. The scaffold has a cylindrical shape having a central axis 2 and includes a pattern of interconnecting structural elements, which will be called bar arms or struts 4. Axis 2 extends through the center of the cylindrical shape formed by the struts 4. The stresses involved during compression and deployment are generally distributed throughout the struts 4 but are focused at the bending elements, crowns or strut junctions. Struts 4 include a series of ring struts 6 that are connected to each other at crowns 8. Ring struts 6 and crowns 8 form sinusoidal rings 5. Rings 5 are arranged longitudinally and centered on an axis 2. Struts 4 also include link struts 9 that connect rings 5 to each other. Rings 5 and link struts 9 collectively form a tubular scaffold having axis 2 represent a bore or longitudinal axis of the scaffold. Ring 5d is located at a distal end of the scaffold. Crowns 8 form smaller angles when the scaffold is crimped to a balloon and larger angles when plastically expanded by the balloon. After deployment, the scaffold is subjected to static and cyclic compressive loads from surrounding tissue. Rings 5 are configured to maintain the scaffold's radially expanded state after deployment.

Scaffolds may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. The scaffold, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorbable or bioresorbable polymer scaffold, as opposed to a metal stent, so that the prosthesis's presence in the vessel is temporary.

Polymeric materials considered for use as a polymeric scaffold, e.g. poly(L-lactide) ("PLLA"), poly(L-lactide-co-glycolide) ("PLGA"), poly(D-lactide-co-glycolide), poly(L-lactide-co-caprolactone), poly(D,L-lactide-co-caprolactone) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to volume ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymer such as PLLA or PLGA.

Intravascular drug eluting scaffolds and stents must fulfill many criteria simultaneously. In addition to the aforementioned acute mechanical demands for radial support, scaffolding, and expansion capability, the stent or scaffold must meet a pharmaceutical function of controlled drug release to prevent neointimal hyperplasia and its consequence of restenosis. While accomplishing this, there are many goals for biocompatibility. Intravascular scaffolds start as blood contacting devices. With time they become encapsulated in the vessel wall where they undergo a benign process of resorption. There is biocompatibility required for blood contact and the necessary compatibility with vascular tissue.

There is a continuing need to improve the biocompatibility of a scaffold; in particular, there is a continuing need to improve upon on the biocompatibility of a scaffold shortly following implantation when a significant portion of the structure is in contact with blood passing through the vessel.

SUMMARY OF THE INVENTION

What is disclosed is a polymeric, bioresorbable scaffold with hemodynamic struts and techniques for making these struts for such a scaffold. The scaffold material includes a bioresorbable, polyester polymer. Scaffolds made in accordance with the invention are balloon-expandable scaffolds configured for being plastically deformed when crimped to a balloon and later expanded from a crimped state by the balloon.

In preferred embodiments, extrusion, injection molding, or dip coating on a mandrel may be used to form a polymer tube. The polymer may be a bioresorbable polymer such as polylactide (PLA) or PLA blended with another polymer, such as polycaprolactone (PCL). The tube may be annealed or expanded/drawn to orient the polymer. Methods are employed, when this tube is made or after making this tube, to vary the wall thickness of the tube over a circumference of the scaffold in accordance with a desired pattern for the scaffold; that is, the wall thickness of the tube is varied in registration to a scaffold pattern. After making the variable wall thickness tube, the scaffold pattern is laser-cut from the tube.

According to one embodiment, regions of high wall thickness in the tube correspond to regions where the highest strains are expected to occur during crimping or balloon expansion of the crimped scaffold. These regions also tend to be where the scaffold experiences the highest degrees of mean and alternating stress during fatigue loading. And regions of low wall thickness in the tube correspond to regions where less strain is expected to occur.

According to another embodiment a scaffold has selectively thickened areas for improving an attachment or retention to the scaffold structure. According to one such embodiment a tube is made to have one or more portions with a higher wall thickness in registration to a scaffold pattern, where the portions correspond to scaffold structure for holding a radiopaque marker.

In one respect the invention provides a scaffold and method for making such a scaffold having improved blood compatibility by reducing a strut height or wall thickness in areas where the added structure is not needed, either to maintain structural integrity or for other reasons, e.g., retain a radiopaque marker in a hole.

Blood compatibility, also known as hemocompatibility or thromboresistance, is a desired property for scaffolds and stents. The adverse event of scaffold thrombosis, while a very low frequency event, carries with it a high incidence of morbidity and mortality. To mitigate the risk of thrombosis, dual anti-platelet therapy is administered with all coronary scaffold and stent implantation. This is to reduce thrombus formation due to the procedure, vessel injury, and the implant itself. Scaffolds and stents are foreign bodies and they all have some degree of thrombogenicity. The thrombogenicity of a scaffold refers to its propensity to form thrombus and this is due to several factors, including strut thickness, strut width, strut shape, total scaffold surface area, scaffold pattern, scaffold length, scaffold diameter, surface roughness and surface chemistry. Some of these factors are interrelated. The effect of strut thickness on acute thrombogenicity has been documented and studied both in vivo and in silico. A scaffold must also occupy a minimum volume as needed to meet the radial strength goals. Consequently, the strut thickness, strut width, and total surface area of a scaffold have multiple constraints, in addition to the influence of these dimensions on its profile and hence its hemocompatibility.

Computational fluid dynamics (CFD) analyses have shown that struts with square cross sections are not ideally hemodynamic and have large recirculating zones both proximal and distal to the strut. FIG. 2 shows a steady-state flow (Re-282) around a square 3a strut. As shown by the arrows there are recirculation zones proximal and distal to the stent strut. Footprints of these zones (KL and MN, respectively) are shown. Shown is a laminar flow condition for the stent strut 3a. The recirculating zones are regions where platelets have long residence time and will be prone to form thrombus.

FIGS. 3A-3B depict experimental results from porcine models for a thin strut (81 microns, μm) and thick strut (162 microns, μm). The drawings, based on images taken from explants (3 days after implantation), show how the in vivo thrombogenicity for the thin struts verses thick struts contributes to the pattern of thrombus formation for porcine coronary arteries (n=6 each). FIG. 4 shows results from a morphometric analysis of adherent thrombus as assessed through luminal area measurement of stented sections of the porcine coronary artery. As shown there is a significant increase in the adherent thrombus when the strut thickness doubles in size. That is, there is a significant increase distally when the strut thickness doubles in size. FIG. 5 is model prediction of the flow alterations surrounding the thin and thick struts (units are cm/sec).

With regards to thrombogenicity of the scaffold in the artery, the most important factors are the minimum lumen diameter (MLD) or diameter of residual stenosis in the scaffold, degree of scaffold malapposition, strut thickness and strut shape. FIGS. 2-5 provide evidence that a strut thickness has a direct effect on its thrombogenicity. Although not the only contributor, thick struts do play a role.

In accordance with the objective of reducing thrombogencity by reducing strut or bar arm wall thickness, a scaffold is cut from a tube having an undulating outer or inner wall surface to produce thick and thin bands or sections arranged circumferentially. Each band extends over the tube length. Each thick band locates crowns and/or links in the scaffold pattern. The thickest portions at the crowns could be 100 microns while the thinnest portions (at a midpoint between crowns) might be 75 microns. Prior to cutting the scaffold pattern the tube is made with these bands that run over the length of the tube (constant cross-sectional profile of the bands with respect to a plane perpendicular to the tube longitudinal axis, e.g., as shown in FIG. 7C). For a pattern such as that shown in FIG. 6A this gives links and crowns a higher thickness than struts (or bar arms).

The variable strut thickness therefore indicates the links being thicker. In preferred embodiments of a scaffold pattern, however, this is not expected to worsen thrombogenicity because a link's longitudinal axes are aligned parallel with the mean direction of blood flow (as opposed to the longitudinal axes of struts or bar arms, which are almost perpendicular to the mean direction of blood flow). Indeed, by making links with the same thickness profile as crowns there should be improved flow over a scaffold with thick crowns and thin links since the link's presence downstream of the crown can reduce backflow or high pressure zones immediately downstream of the crown. Moreover, link thickness is beneficial from a strength perspective, as follows. In designing bioresorbable scaffolds links are sometimes designed to be quite narrow in order to have a small crimped profile. This can make the links more prone to fracture during delivery and fatigue so being relatively thicker could be structurally advantageous. Thinner wall thickness exists at the bar arms or struts connecting crowns, which is beneficial for more rapid reendothelialization and reduced acute thrombogenicity since when deployed, they are more oriented at right angles to the blood flow. Strut thickness nearer to the crown may be made higher to maintain scaffold radial strength.

One method to produce the variable thickness after expansion is by longitudinally machining the outer wall surface of a tube. A tube would is placed on a mandrel for support. This assembly is fixed in a chuck. The rest of the tubing is held in a precision milling machine with a rotating cutter which may be programmed under numerical control to cut one thin region (struts) and two adjacent halves of a thick region (crowns and links) at once. After making one longitudinal cut, the tubing is rotated the necessary amount, and another cut is made. This operation is repeated for each tube that will be used to make scaffolds. In preferred embodiments tubes that are strengthened by one or both of a blow molding or drawing process are used. Instead of machining by cutting or scrapping the outer wall of the tube to remove material, a laser may be used to ablate or vaporize material. Yet another methodology would be to injection mold the tube with the shape of the mold imposing the variable thickness morphology.

Another method for making a variable wall thickness tube is to apply a mask or use eccentric lighting (heat lamps or multiple infra-red (IR) lasers) to vary heat distribution over the circumference of the tube during a blow molding process. It has been found that by intentionally creating local hot or cold spots one can cause the thickness of the tube to vary circumferentially and precisely enough to be in registration with the locations of crowns and struts and the desired thickness variation. In one embodiment a uniform heat source for the tubing is applied, such as by using two curved bulbs. A precision cylindrical mask is interposed between the lamps and the glass mold. The mask would contain a series of longitudinal slits, holes to vary the light transfer in a circumferential manner. The mask could be made of metal. Or the mask could be made of a transparent material and be tinted, colored or painted in a circumferentially varying manner. In an alternative embodiment local heat sources can be applied strategically to introduce controlled thick spots around the tubing circumference with an indexing scheme in order to make crown locations thicker than strut locations.

In accordance with these objectives, there is a method for making a scaffold from a tube having a variable wall thickness, a scaffold having a variable wall thickness, making a tube having variable wall thickness, a medical device comprising such a scaffold, or a method for assembly of such a medical device having one or more, or any combination of the following concepts (1) through (17):

(1) a polymer scaffold made from a tube;
(2) An aspect ratio (AR) of strut width (w) to wall thickness (t) (AR=w/t) is between 0.5 to 1.5, 0.7 to 1.5, 0.7 to 1.3, 0.9 to 1.5, 0.9 to 1.2, 1.0 to 1.5 or 1.5 to 2.0;
(3) A wall thickness for a scaffold (pre-crimp diameter of 3 to 4 mm) is less than 150 microns, less than 140 microns, less than 130 microns, about 100 micron, 80 to 100 microns, 80 to 120 microns, 90 to 100 microns, 90 to 110 microns, 110 to 120 microns, or 95 to 105 microns. More preferably a wall thickness is between 80 and 100 microns, and more preferably between 82 and 89 microns;
(4) A wall thickness for a scaffold (pre-crimp diameter of 5 to 10 mm) is less than 280 microns, less than 260 microns, less than 240 microns, about 190 micron, 149 to 186 microns, 149 to 220 microns, 170 to 190 microns, 170 to 210 microns, 210 to 220 microns. More preferably a wall thickness is between 150 and 190 microns for a scaffold having an outer diameter of 7, 8 or 9 mm;

(5) The scaffold has a pattern as described in US20100004735 at FIGS. 2, 4, 5A, 5B, 5C, 5D and paragraphs [0043]-[0062]. Or the scaffold has a pattern as described in US20110190872 at FIGS. 4, 5A, 6A, and paragraphs [0126]-[0130];

(6) For a maximum wall thickness t-max (or t1), and minimum wall thickness t-min (or t2), the ratio of t-max to t-min, or the quotient (t-max/t-min) is about 2, or between 2 and 1.2, or about 1.3. For example, t-max is equal to 158 microns and t-min is equal to 93 microns. In some embodiments t-max is equal to 120 to 130 microns and t-min is equal to 90 to 100 microns; t-max is about 100 microns, t-min is about 75 microns, t-min is between 75 and 85 microns, and t-max is between 90 and 100 microns;

(7) The outer wall surface is undulating to provide a variable wall thickness scaffold; or the inner wall surface is undulating to provide a variable wall thickness scaffold, or both the outer and inner wall surface is undulating to provide a variable wall thickness scaffold;

(8) The outer wall surface or the inner wall surface of the scaffold has a repeating pattern according to FIG. 6C or 8B over the circumference;

(9) The outer wall surface or inner wall surface has an undulating pattern as described in any of the embodiments discussed in connection with FIGS. 6B-6C, or any of the embodiments discussed in connection with FIGS. 7A-7B;

(10) The tube is blow-molded to form an undulating inner wall surface, wherein a temperature difference of 5 Deg. Celsius to 50 Deg. Celsius between a hot and cold part of the tube exists when the tube is being radial expanded; or there is a temperature gradient of between 10 Deg. C./mm and 200 Deg. C./mm between a circumferential location corresponding to a crown center and a location corresponding to a midpoint of a strut;

(11) A scaffold having a higher wall thickness for a marker link than an adjacent link not holding a marker;

(12) A scaffold having a higher wall thickness for a pair of links spaced 180 degrees apart than all other links disposed between the links spaced 180 degrees apart and located anywhere along the scaffold longitudinal axis;

(13) A scaffold having a wall thickness of at least 120 microns for a link holding a radiopaque marker and crowns connected to the link, and between 80 and 110 microns for a plurality of struts and links adjacent the link holding the marker and the crowns connected to the link and holding the marker;

(14) A scaffold having rings connected by links, the rings including struts interconnecting crowns, wherein the links extend parallel to the longitudinal axis and between crowns, and wherein the crowns and links having a wall thickness that is between 1.2 and 2 times a wall thickness for struts;

(15) A process for making a tube according to the processing parameters of TABLE 1;

(16) A medical device, comprising: a tubular body made from a polymer material, the tubular body having one of an undulating inner wall surface and an undulating outer wall surface such that a ratio of a maximum wall thickness (t-max) to a minimum wall thickness (t-min) for the tubular body is between 2 and 1.2; wherein the one of an undulating inner wall surface and an undulating outer wall surface comprises a curved surface that repeats every 20, 30, 45, or 180 degrees about a circumference of the tubular body; and/or

(17) The medical device of (16) including one or more of, or any combination of items (a) through (t):

(a) wherein the tubular body is a scaffold having interconnected elements comprising a first ring connected to a second ring by a link, wherein the first and second rings have crowns interconnected by struts, and wherein for the curved surface that repeats every 20 degrees the first and second rings have 18 crowns, wherein for the curved surface that repeats every 30 degrees the first and second rings have 12 crowns, wherein for the curved surface that repeats every 45 degrees the first and second rings have 8 crowns, (b) wherein the curved surface is described by one period of a sinusoid, a portion of the curved surface is parabolic, or a portion of the curved surface is hyperbolic, (c) wherein the curved surface is concave between rings, (d) wherein the curved surface is convex between struts, (e) wherein the curved surface comprises a first curvature centered over a crown and a second curvature centered over a midpoint between crowns, and wherein the first curvature is less than the second curvature, (f) wherein the curved surface comprises a first curvature centered over a crown and a second curvature centered over a midpoint between crowns, and wherein the first curvature is greater than the second curvature, (g) wherein the wall thickness is t-max at the crowns and the wall thickness monotonically decreases from t-max to t-min, wherein a strut midpoint has a wall thickness of t-min, (h) wherein the links are arranged parallel to a longitudinal axis of the scaffold and have a wall thickness t-max, and a width less than a strut width to reduce occurrence of backflow downstream of a crown when the scaffold is implanted within a vessel and to reduce a crimped diameter for the scaffold, (i) wherein crowns and links have a wall thickness of t-max and the struts have a wall thickness of t-min, (j) wherein t-max and t-min are one of: 250 and 150 microns, respectively; 100 microns and 75 microns, respectively; 130 microns and 90 microns, respectively; or 150 microns and 100 microns, respectively, (k) wherein t-max is between 160 and 130 microns or 130 and 100 microns, (l) wherein t-min is between 100 and 75 microns or 90 and 70 microns, (m) wherein the other of the outer wall surface and the inner wall surface describes a cylinder, (n) wherein the medical device comprises a composition including poly(l-lactide), (o) wherein the tubular body is a biaxial expanded tubular body, (p) wherein the tubular body is a scaffold having interconnected elements comprising a first ring connected to a second ring by at least a first and second link, and the second ring is connected to a third ring by at least a third and fourth link, wherein the curved surface repeats every 180 degrees, the first and second links hold a radiopaque marker, the first and second links have a wall thickness of t-max, and the second and third links have a wall thickness of t-min, (q) wherein the undulating wall surface is the outer wall surface of the tubular body, the method comprising: making a cylindrical tube having a longitudinal axis, and removing strips of material from the outer wall, wherein the removed strip extended over a length of the tube, and wherein a cross-section of the removed strip is constant over the longitudinal axis such that the cross-sectional shape of the tube having the undulating outer wall surface is constant along the longitudinal axis, (r) wherein the undulating wall surface is the inner wall surface of the tubular body, a method comprising radially expanding a cylindrical tube within a mold, wherein the cylindrical tube is heated to create a temperature gradient about the tube circumference and hot and cold spots during expansion within the mold, and wherein a wall thickness of t-min for the medical device corresponds to a hot spot and a wall thickness of t-max for the medical device corresponds to a cold spot, and/or (s) wherein the radially expanded tube has a temperature difference between a first location and a second location of 5 to 50 Deg. Celsius.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

Definitions

Figure 1:
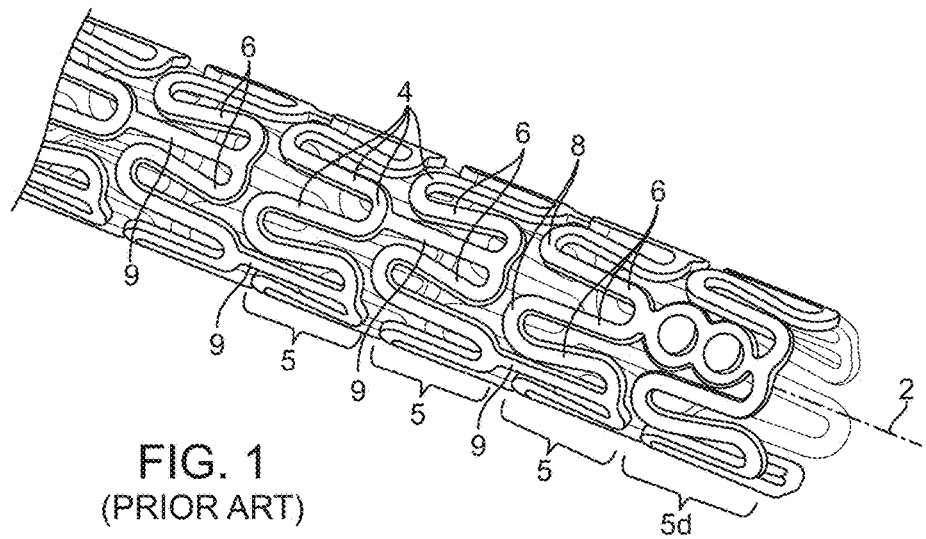
FIG. 1 is a perspective view of a portion of a prior art scaffold. The scaffold is shown in a crimped state (balloon not shown).
Figure 2:
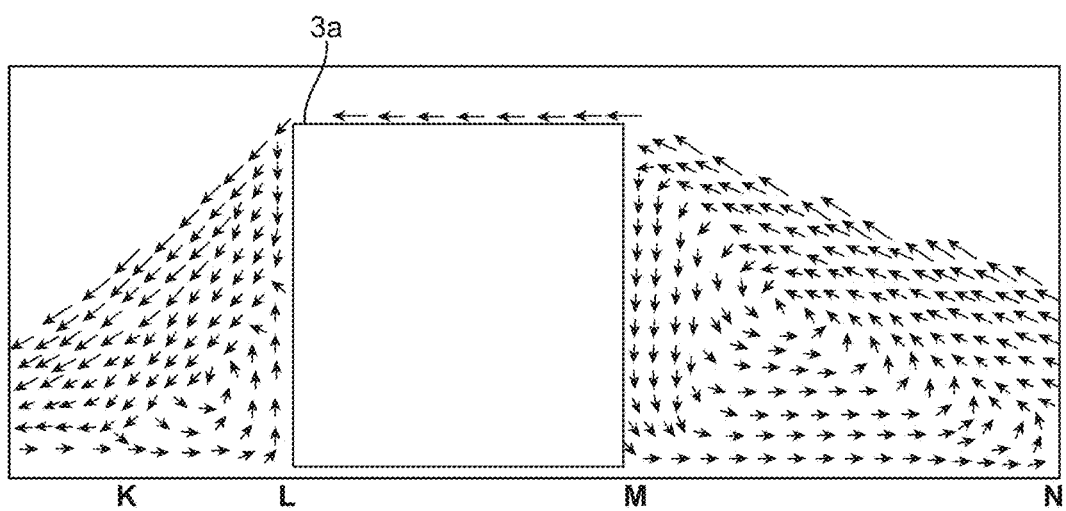
FIG. 2 shows fluid streamlines adjacent a square-cross-section of a scaffold strut. The streamlines show zones of fluid recirculation upstream and downstream of the strut.
Figures 3A, 3B:
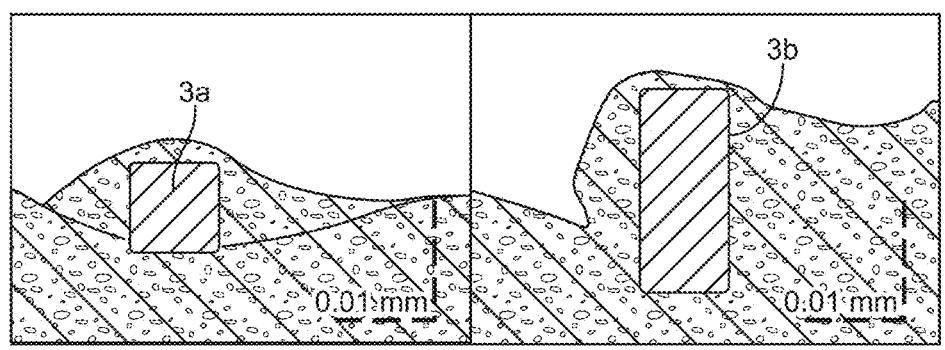
FIG. 3A is a cross-sectional view of a thin strut of scaffold based on an explant of an implanted scaffold from a porcine model.
FIG. 3B is a cross-sectional view of a thick strut of scaffold based on an explant of an implanted scaffold from a porcine model.

In the description like reference numbers appearing in the drawings and description designate corresponding or like elements among the different views.

For purposes of this disclosure, the following terms and definitions apply:

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

A "stent" means a permanent, durable or non-degrading structure, usually comprised of a non-degrading metal or metal alloy structure, generally speaking, while a "scaffold" means a temporary structure comprising a bioresorbable or biodegradable polymer, metal or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon (i.e., a balloon having a 6.5 mm nominal diameter when inflated to a nominal balloon pressure such as 6 times atmospheric pressure) has about a 7.4 mm post-dilation diameter, or a 6.0 mm balloon has about a 6.5 mm post-dilation diameter. The nominal to post dilation ratios for a balloon may range from 1.05 to 1.30 (i.e., a post-dilation diameter may be 5% to 30% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold. For a deployed scaffold the PDD is usually the inner diameter of the scaffold.

A "pre-crimp diameter" means an outer diameter (OD) of a tube from which the scaffold was made (e.g., the scaffold is cut from a dip coated, injection molded, extruded, radially expanded, die drawn, and/or annealed tube) or the scaffold before it is crimped to a balloon. Similarly, a "crimped diameter" means the OD of the scaffold when crimped to a balloon. The "pre-crimp diameter" can be about 2 to 2.5, 2 to 2.3, 2.3, 2, 2.5, 3.0 times greater than the crimped diameter and about 0.9, 1.0, 1.1, 1.3 and about 1-1.5 times higher than an expanded diameter, the nominal balloon diameter, or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 1. When the scaffold is deployed or expanded by the balloon, the inflated balloon plastically deforms the scaffold from its crimped diameter. Methods for crimping scaffolds made according to the disclosure are described in US20130255853.

Figure 6A:
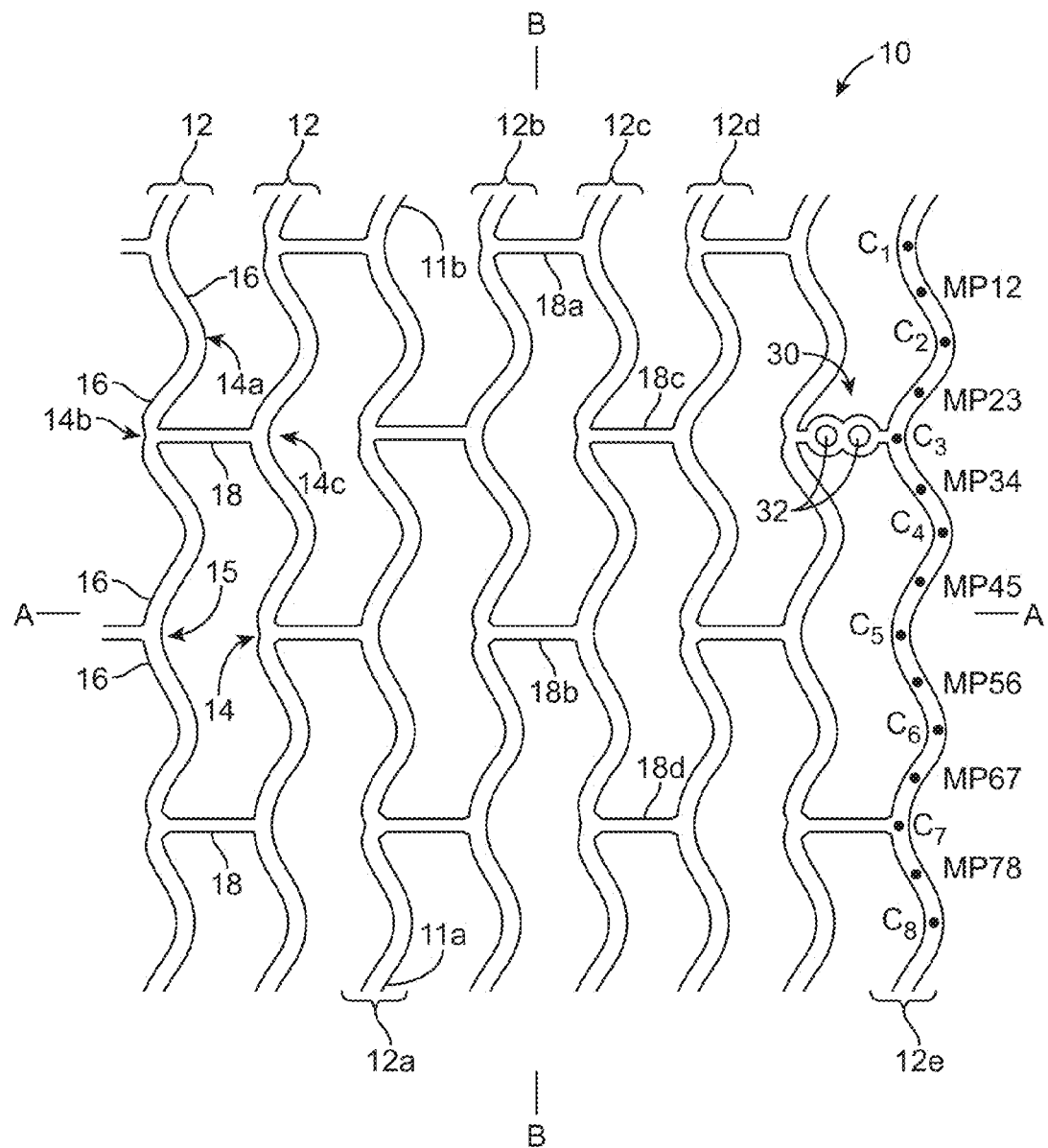
FIG. 6A is a flattened, planar view of a portion of a scaffold showing a scaffold pattern of rings interconnected by links.
Figure 6B:
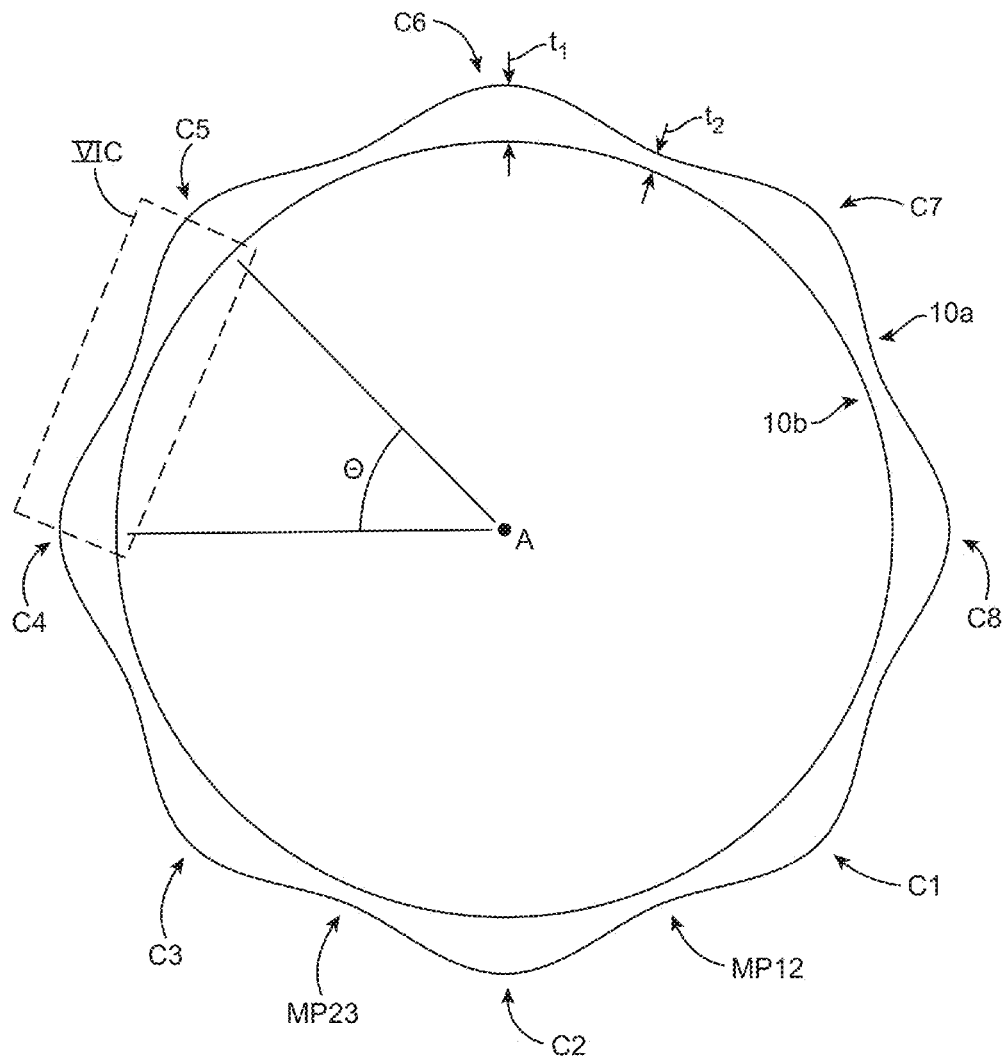
FIG. 6B is a cross-sectional view of the scaffold of FIG. 6A and a showing a variable wall thickness of the scaffold. The view of FIG. 6B is taken perpendicular to a longitudinal axis or along line A-A of the scaffold of FIG. 6A.
Figure 6C:
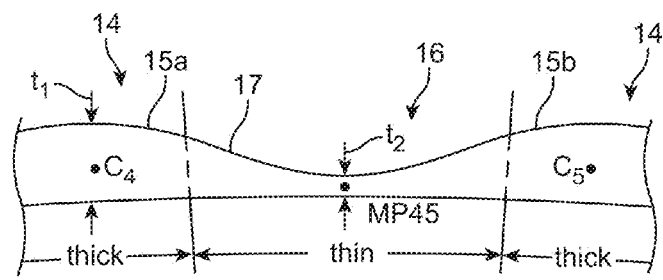
FIG. 6C shows in close-up a portion IVC of the scaffold in FIG. 6B.

An "undulating inner wall surface" or "undulating outer wall surface" of a tube or scaffold means an outer wall surface that is not an arc of a circle, or a surface of a cylinder. The undulating surface varies in periodic fashion over the outer wall of a tube or scaffold, e.g., every 20, 30 or 45 degrees. One example is a sinusoidal undulating surface that repeats every 20, 30 or 45 degrees. The repeating undulating surface may also vary in a fashion that is not purely sinusoidal but approximated in part by an arc of a circle (having a same or smaller radius of curvature than the outer or inner radius of the scaffold/tube at a crown center or midpoint of a strut), a parabolic surface or a hyperbolic surface. These two alternative outer surface shapes may describe the surface about the crown or on each side of the crown, respectively. Referring to FIGS. 6A, 6B and 6C there is shown a planar, cross-sectional, and partial cross-sectional view, respectively, of a scaffold 10 according to one aspect of the disclosure. The scaffold is made from a tube processed to have a variable wall thickness. The variable wall thickness is made in registration with a selected pattern for the scaffold 10.

Referring to FIG. 6A there is shown an example of the scaffold 10 having ring elements 12 interconnected by link elements 18. Each ring 12 has crown elements, or crowns 14 interconnected by strut elements, or struts 16. The line A-A in FIG. 6A is collinear with a longitudinal or bore axis for the scaffold 10. The line B-B extends about the circumference of the scaffold 10 (FIG. 6A is a flattened view of the scaffold in the horizontal plane to show the pattern). The partial struts shown along the upper edge of FIG. 6A correspond to the same partial struts shown along the lower edge of FIG. 6A. Thus, element 11a is the same as element 11b for ring 12a.

The scaffold 10 has eight crowns 14 per ring 12 and two links 18 connect a ring to an adjacent ring. Each link 18 connects to a crown 14 at a W-crown and a Y-crown. A "W-crown" refers to a crown where the angle extending between a strut 16 and the link 18 at the crown is an acute angle (less than 90 degrees). A "Y-crown" refers to a crown where the angle extending between a strut 16 and the link 18 at the crown 14 is an obtuse angle (greater than 90 degrees). Crown 14a is an example of a U-crown, which is not connected to a link 18. Crown 14b is an example of a W-crown. And Crown 14c is an example of a Y-crown.

Ring 12b connects to ring 12c through link elements 18a and 18b, which connect to ring 12b at W-crowns and ring 12c at Y-crowns. There is one U-crown between every Y-crown and W-crown of rings 12a and 12b. Ring 12c connects to ring 12d through link elements 18c and 18d, which connect to ring 12c at W-crowns and ring 12d at Y-crowns. There is one U-crown between every respective Y-crown and W-crown of rings 12c and 12d.

Referring to the end ring 12e, there is designated crown numbers C1, C2, C3, C4, C5, C6, C7 and C8. These same crown numbers apply to the crowns of other rings, as follows. A crown of one ring has the same crown number as a crown of any other ring when the crown is located at the same circumferential location, or location on the line B-B in FIG. 6A, as the other rings 12. A crown for one ring is therefore differentiated from the crown for another ring based on its location along the line A-A.

A midpoint or mid-distance between adjacent crowns is also indicated in FIG. 6A by the abbreviation "MPnm" where "n" and "m" refer to the adjacent crowns. The mid-distance or midpoint MPnm is located at half the distance from the geometric center of the adjacent crowns, or the midpoint between adjacent crowns. The midpoint may also be understood as the geometric center (or centroid) of the strut 16 that extends between the crowns. The midpoint between crowns C1 and C2 is indicated as MP12, the midpoint between crowns C2 and C3 is indicated as MP23, the midpoint between crowns C3 and C4 is indicated as MP34, etc. The same numbering convention applies for midpoints between the other crowns for scaffold 10.

Referring to FIG. 6B there is shown a view of the scaffold of FIG. 6A looking down the axis A-A or perpendicular to the longitudinal axis of the scaffold 10. The crown numbers C1-C8 for end ring 12e are shown.

The scaffold has a circular inner wall surface or constant inner diameter. The outer wall surface varies, due to the outer surface being wavy or undulating. The outer wall surface 10a and circular inner wall surface 10b have the combined effect of producing a varying wall thickness about the circumference of the scaffold. The variation in wall thickness is constant along the longitudinal axis. Each of the rings 12 of the illustrated scaffold 10 therefore have the same shape as shown for ring 12e in FIG. 6B. The scaffold 10 wall thickness is thickest at crowns C1-C8 and thinnest at the midpoints MPnm between crowns. The thickness at each crown is designed by t1 in FIG. 6B and the thickness at the midpoint is designated by t2. The ratio of t1 to t2, or the quotient t1/t2 is about 2. For example, t1 is equal to 158 microns or about 100 microns, and t2 is equal to 93 microns or about 75 microns. In some embodiments t1 is equal to 120 to 130 microns and t2 is equal to 90 to 100 microns.

Figure 4:
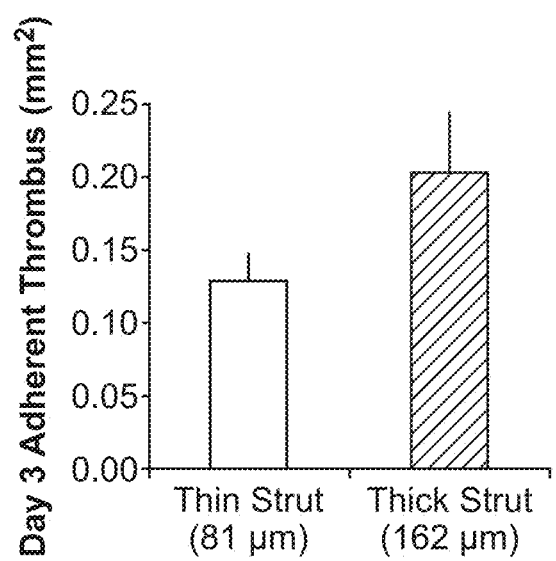
FIG. 4 compares the Adherent Thrombus property of the thin verses thick struts depicted in FIGS. 3A and 3B.
Figure 5:
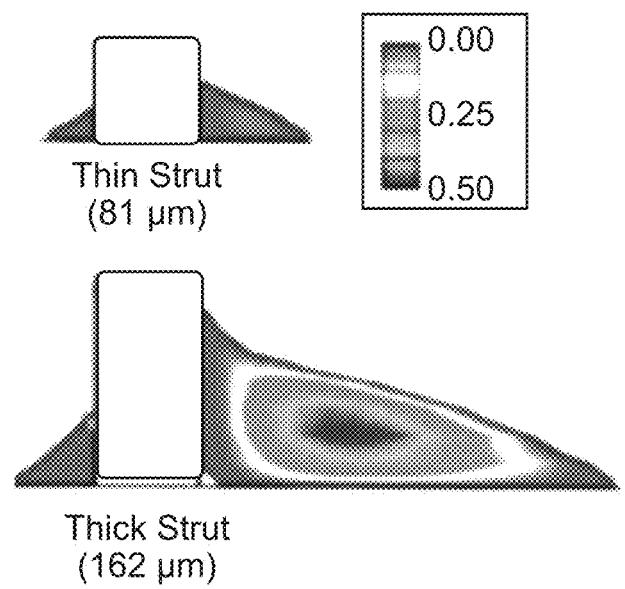
FIG. 5 describes, using a mathematical model, fluid flow immediately upstream and downstream of thin and thick struts for a scaffold.

The variance in wall thickness or undulating outer wall surface for the scaffold 10 is periodic over θ degrees between crowns, or the curved surface segment ("curved surface") for the outer wall repeats every 360/NC degrees where NC is the number of crowns in a ring. Thus, the curved surface repeats every θ=45 degrees for the illustrated 8 crown ring and every θ=30 degrees for a 12 crown ring. As an example of the scaffold having 12, instead of the illustrated 8 crowns (FIG. 6B), and also considered part of this disclosure is the scaffold pattern described in US20100004735 at FIGS. 2, 4, 5A, 5B, 5C, 5D and paragraphs [0043]-[0062]. The curved surface repeats every θ=20 degrees for an 18 crown ring. As an example of a scaffold having 18 crowns and also considered part of this disclosure is the scaffold pattern described in US20110190872 at FIGS. 4, 5A, 6A, and paragraphs [0126]-[0130].

Referring to FIG. 6C there is shown in close-up the portion VIC of the ring 12e between crowns C4 and C5 from FIG. 6B. The curved surface described in FIG. 6C is the same as elsewhere over the outer wall surface for the scaffold 10. The portions corresponding to the crowns C4, C5 are designated as "thick" and the portion corresponding to the strut 16 having midpoint MP45 and extending between the crown C4 and C5 is designated as "thin." The crown or "thick" part is that part of a ring where the curved surface corresponding to an outer or inner radius of the crown 14 exists (FIG. 6A), as opposed to a straight surface of a strut 16 (FIG. 6A).

The outer surface extending between the crowns C4, C5 may be described as follows. The surfaces 15a, 15b at the crown are rounded (or have no sharp corners) and are symmetric about the geometric center C4, C5 of the crown. Or the surfaces at the crown are rounded (or have no sharp corners) and symmetric about the idealized hinge point C4, C5 for the crown, i.e., the theoretical point that the strut 14 on each side of the crown rotates about in FIG. 6A when the ring 12e is reduced in size or expanded during plastic deformation (crimping/balloon inflation from the crimped state). The thickness t1 over surface 15a is about the same, or varies from 5 to 10% from the thickness t1 at the center C4, C5.

The strut 16 surface 17 extending between the surfaces 15a, 15b is convex, a continuously curved surface between the crowns, and/or monotonically decreases from left to right or right to left in FIG. 6C from the surface 15a and 15b, respectively, to the midpoint that has the wall thickness t2. One example is a sinusoidal undulation periodic over the arc length between crown centers. The surface 17 according to other embodiments is defined by a radius of curvature, i.e., the convex shape follows the arc of a circle centered equidistant between the crowns, C4, C5, with the surface 17 being continuous with surfaces 15a, 15b to avoid sharp edges that can lead to stress concentrations during loading. Surface 17 may be sinusoidal. Alternatively, surface 17 may include a parabolic shape centered about the midpoint MP45 and extending to near to, or to the crowns C4, C5 on each side of the midpoint MP45. The surface 17 may also have a hyperbolic shape extending between the midpoint MP45 and crowns C4, C5. And the curvature at the midpoint MP45 may be the same as, less than or greater than the curvature at the crowns C4, C5.

Figure 6D:
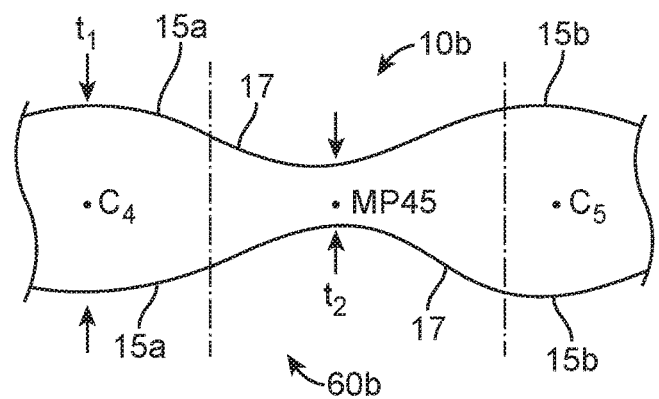
FIG. 6D shows in close-up the portion IVC of a scaffold having an undulating outer surface and an undulating inner surface according to another embodiment.
Figure 6E:
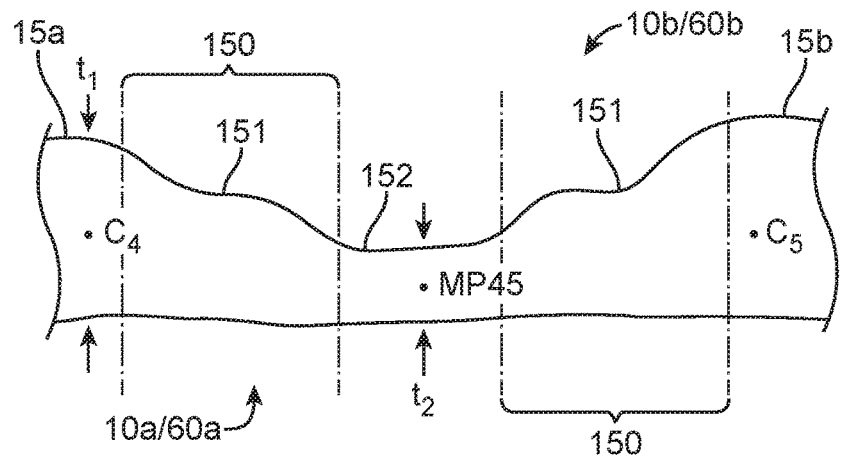
FIG. 6E shows in close-up the portion IVC of a scaffold having an undulating outer surface or an undulating inner surface according to another embodiment.
Figure 6F:
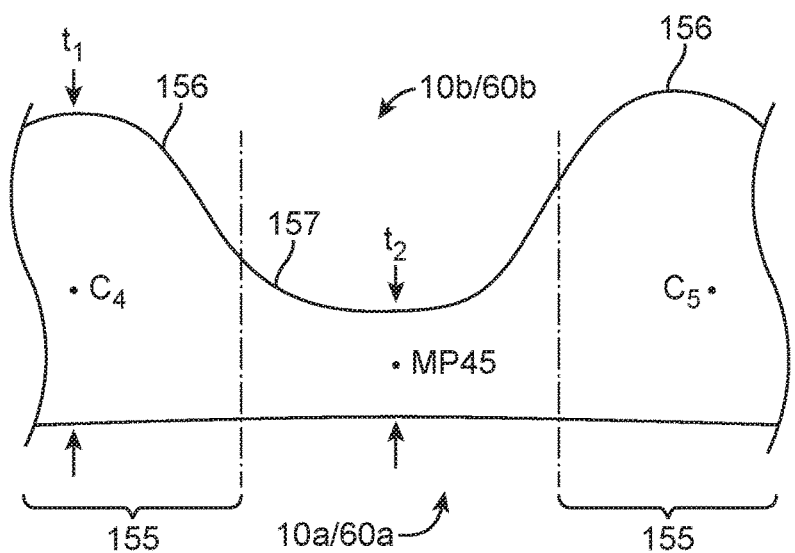
FIG. 6F shows in close-up the portion IVC of a scaffold having an undulating outer surface or an undulating inner surface according to another embodiment.

Referring to FIGS. 6D, 6E and 6F there are shown alternative embodiments of a scaffold having undulating outer surfaces and/or inner surfaces. FIG. 6D shows a scaffold repeating section where both the inner and outer surfaces are undulating surfaces, for example, both are sinusoidal. Both or either of the undulating inner and outer surfaces of FIG. 6D may, in other embodiments, correspond to any of the outer surfaces described earlier in connection with FIG. 6C or the undulating inner surface described in connection with FIG. 8B, infra. FIGS. 6E and 6F show a repeating section of a scaffold where undulating surfaces are, in part, described by hyperbolic or parabolic shapes, respectively.

FIG. 6E shows undulating surfaces 151 that are hyperbolic between the strut midpoint MP45 and crowns C4, C5. The hyperbolic outer surface portion is also indicated by 150. The strut surface 152 and surfaces 15a, 15b at crown centers may have a surface described by a radius of curvature as discussed earlier.

FIG. 6F shows surfaces 156 that are parabolic. The parabolic portion 155 of the undulating outer surface would be centered about each crown, as shown. The surface 157 extending between parabolic surfaces 156 may be described by a radius of curvature as discussed earlier.

Referring again to FIG. 6A, each of the link elements 18 extending between the rings 12 have the same thickness t1 as at the crowns. In one particular embodiment the thickness t1 is chosen to improve the retention of a radiopaque marker in a link element. Such a link element is illustrated in FIG. 6A as link 30, which has holes formed in it to hold radiopaque markers 32. For embodiments having a thickness t1 to improve retention of the marker 32 in the hole the thickness is between 120 and 150 microns, about 125 microns, or up to 160 microns. According to another embodiment of a scaffold for increasing retention of a marker, a tube is made to have only one, or two thick parts. These thick parts correspond to links where the markers will be held in the scaffold cut from the tube. For example, the thick parts corresponding to one or both of crowns C3 and C6. Alternatively, the tube is made to have only two thick parts separated by 180 degrees. According to these embodiments the scaffold has a wall thickness of about 80 to 100 microns everywhere, except for the region between strut midpoints surrounding links where a marker will be held on the scaffold. There a wall thickness of at least 120 microns is made.

A method for making the scaffold of FIGS. 6A-6C is described next.

Figure 7A:
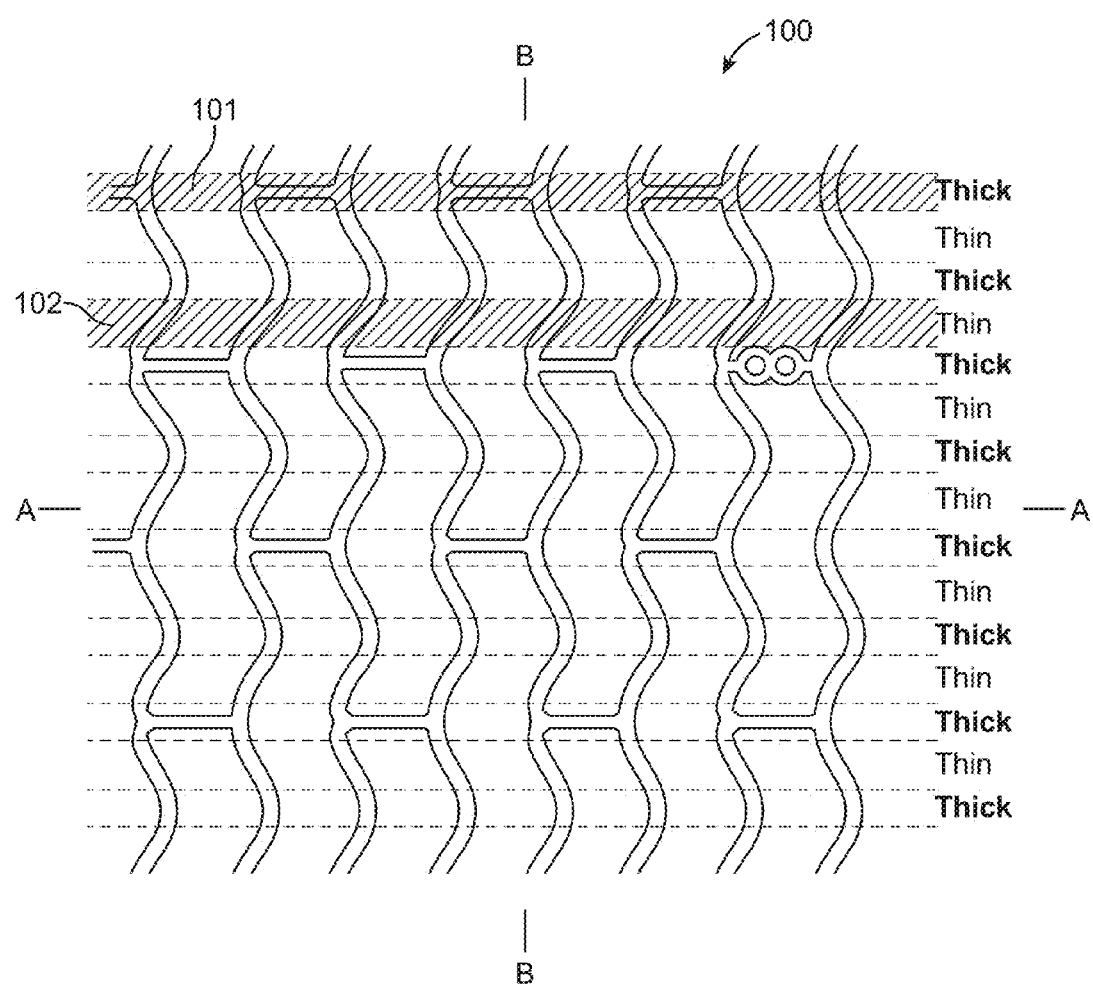
FIG. 7A is the flattened, planar view of the scaffold from FIG. 6A but with lines indicating areas of thick or thin wall thickness.

Referring to FIG. 7A there is shown the planar view of the scaffold 10 with registration lines (dashed lines) indicating the pattern 100 of cutting of a polymer tube to register the areas of high thickness (shaded area 101 for example) and low thickness (shaded area 102 for example) corresponding to where the crowns and struts, respectively, will be located when the pattern is cut from the tube. As indicated, the sections of the tube that will have a higher thickness (t1) are indicated as "thick" and the sections having the lower thickness (t2) are indicate as "thin." Additionally, the bands of "thick" wall thickness 101 and "thin" wall thickness 102 are constant in cross section, i.e., the cross-section as viewed in the plane perpendicular to the longitudinal axis or line A-A.

The information in FIG. 7A, along with the rate of change or curvature between the center of a crown and center of a strut that repeats between crowns, may be registered with a numerically controlled machine, e.g., a lathe 50 shown in FIG. 11, to cut the tube that will be later formed into the scaffold 10 having the pattern of rings and connecting links shown in FIGS. 6A-6C.

Thus, after the tube is made the scaffold 10 pattern is registered in respect to the locations of the crowns and struts of rings 12, the minimum and maximum thickness of those sections, curvatures of the outer surface for thick and thin parts and/or the shape of the curve between peaks, e.g., sinusoidal or arc of a circle over the length of the strut then continuous, rounded curve at crown or flat peak with rounded edges, and this information is fed into a numerical controlled machine for controlling a cutting piece for making the contoured outer surface of a tube. After making this contoured surface, the scaffold pattern may be laser cut using standard techniques well known in the art. Laser cutting a bioresorbable polymer scaffold where the wall or strut thickness varies within the scaffold pattern may require some modification of laser cutting parameters compared to those used to cut a scaffold of uniform strut thickness. The interaction of the varying strut thickness with the laser focal point may be accommodated using focusing optics with a lower numerical aperture with larger depth of field or choosing a focal point that is a compromise between the halfway point through the thin and thin wall thickness. Thicker tubing can often require higher laser power to cut fully through when a single pass process is being used. An alternative is to vary the linear speed of the laser cutter so that it is faster in the thinner regions and slower in the thicker ones.

Figure 7B:
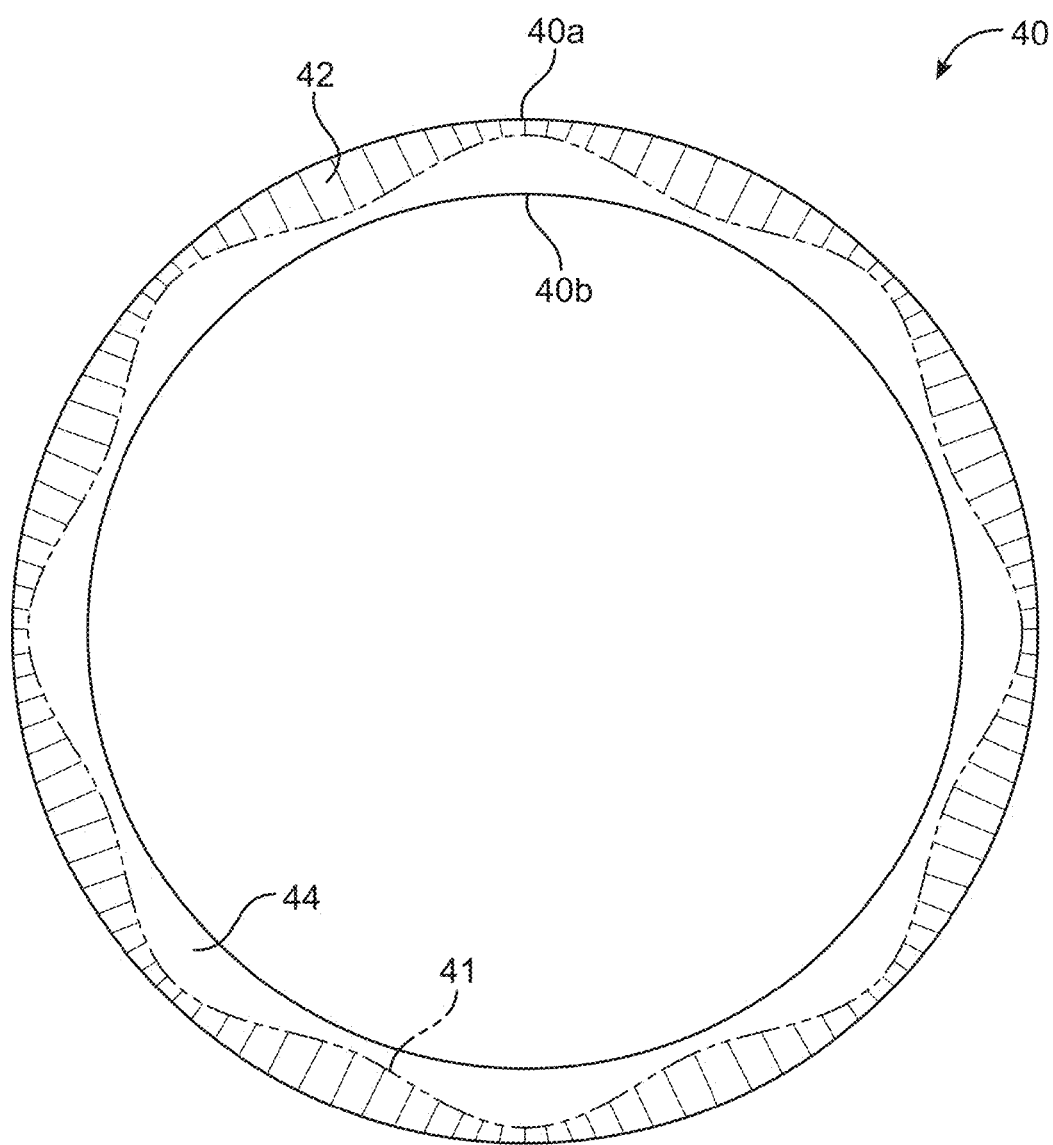
FIG. 7B is a cross-sectional view of a tube used to make the scaffold of FIGS. 6A-6B, prior to modifying the outer wall to have the undulating surface shown in FIG. 6B.

Referring to FIG. 7B there is shown a cross-sectional view (perpendicular to longitudinal axis) of a polymer tube 40 prior to making the outer curved surface. The outer and inner surfaces 40a, 40b of the tube describe a cylindrical surface. A pattern 41 for making the contoured outer surface is shown in phantom. The contoured surface is made, according to one embodiment, by removing the shaded material 42, which extends longitudinally over the length of the tube 40, leaving the body 44 that is then laser cut into the scaffold pattern of FIG. 6A. The shaded areas may be thought of as grooves. Extending lengthwise over the tube. In some embodiments both the thick parts 101 and thin parts 102 (FIG. 7A) are cut away. In other embodiments the tube has a thickness t1 when made and only edges of the thick parts 101 are cut to make a smooth transition to thin parts.

As mentioned above, the material 42 removal according to the pattern 41 may be accomplished using a numerically controlled cutting tool, such as a numerically controlled lathe having a cutting piece. The tube 40 is mounted on a mandrel and a cutting piece is moved around the tube 40, or the tube is rotated under the cutting piece to form the contoured outer surface.

The cutting piece may be a rotating cutter which comprises one "period" or undulation of surface 41. Such a rotating cutter may be made of hardening tool steel cobat alloy, or any one of a number of hard metal alloys. A rotating cutter would be moved relative to the tube in a longitudinal fashion to cut one groove along the tube length. The cutter or tube would then be repositioned and another groove cut. In one embodiment, the axis of the rotating cutter is perpendicular to the cylindrical axis of the tube, but tangent to the tube circumference. However, in another embodiment, the rotational axis of the cutter is perpendicular to the cylindrical axis of the tube and perpendicular to the tube surface.

In another embodiment, the cutting piece extends over the length of the tube 40 so that all material 42 over the tube 40 length is removed at the same time. As an alternative to a cutting piece, the material 42 may be removed by ablation using a laser, or by a plume of abrasive material directed at the tube surface.

Figure 11:
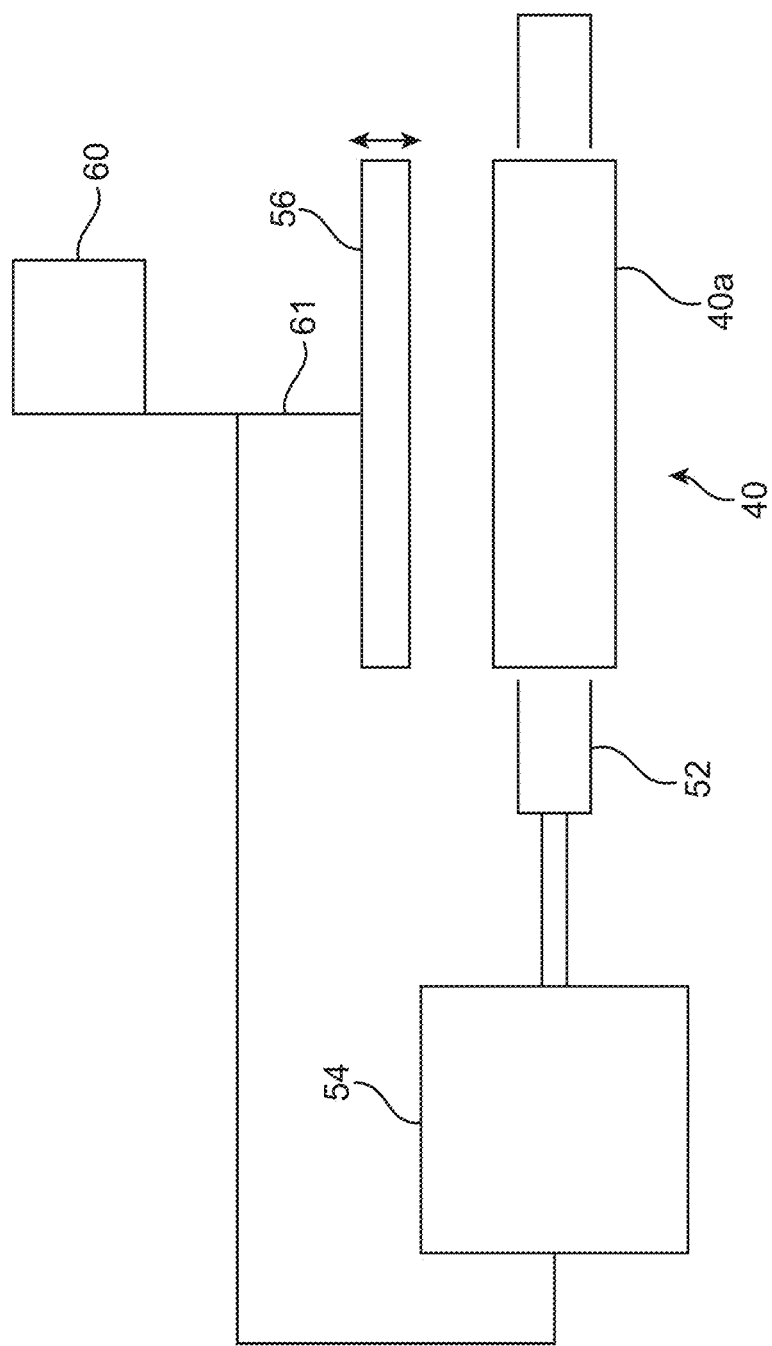
FIG. 11 shows an assembly for modifying the outer surface of a tube in the manner shown in FIG. 7C.

FIG. 11 shows an embodiment of a lathe with the tube 40 secured to a mandrel 52, motor 54 for rotating the mandrel 52 about the longitudinal axis, and a cutting piece 56 configured for cutting along the entire length of the tube 40 as the cutting piece 56 is moved onto the tube 40 surface (alternatively, a laser may be used to remove material from tube 40). The cutting piece 56 and motor 54 are controlled by a numeric controller 60. The tube 40 is held in a chuck (not shown). The controller 60 sends control signals to the motor 54 to control its rotation rate while an actuator 61 is controlled to raise and lower the cutting piece 56 to control the depth of the cut into the tube outer surface 40a. During machining it is desirable to control the tube temperature to prevent it from softening excessively or becoming tacky. Allowing the tube to warm above its Tg can lead to residual stresses in the tube from expansion inducing tube shrinkage. Cooling gas jets can be used to cool the tube. The entire apparatus can be placed in a temperature controlled chamber to assure the polymer stays below its Tg. The tube 40 may be made by extrusion, 3-D printing, injection molding, or dip coating on a mandrel. The tube material is a bioresorbable polymer such as polylactide (PLA) or PLA blended with another polymer, such polycaprolactone (PCL). The tube may be annealed or expanded/drawn to orient the polymer. The wall thickness of the tube may be t1, or greater than t1. In the former case the contoured outer surface would be made without removing material at the center of the crown (thick strip 101 from FIG. 7A) and in the latter case material is removed for strips 101 and 102 to arrive at the thickness t1 at crowns and t2 between crowns.

Figure 7C:
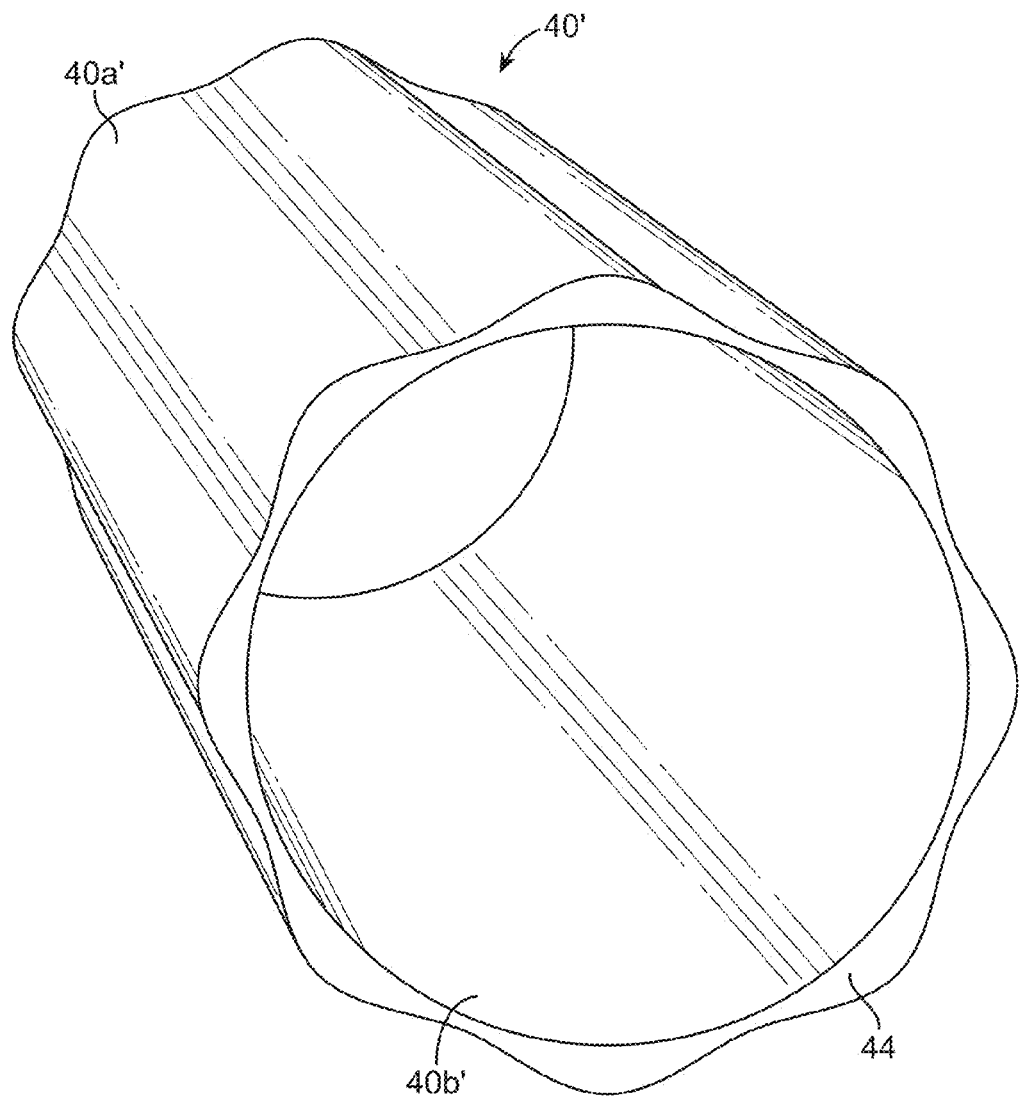
FIG. 7C is a perspective view of the tube of FIG. 7B after modifying the outer wall.

Referring to FIG. 7C there is shown a perspective view of the tube 40' after the tube 40 is machined using the lathe 50 to remove the shaded material 42 (FIG. 7B). The tube 40' has a contoured outer surface 40a' which shows the removed material along the length of the tube, thereby leaving material 44. The inner surface 40b' is unchanged. The scaffold pattern for scaffold 10 may be laser cut from the tube 40' to produce scaffold 10 using standard techniques well known in the art. Laser cutting a bioresorbable polymer scaffold where the wall or strut thickness varies within the scaffold pattern may require some modification of laser cutting parameters compared to those used to cut a scaffold of uniform strut/wall thickness. The interaction of the varying strut thickness with the laser focal point may be accommodated by using focusing optics with a lower numerical aperture having a larger depth of field or choosing a focal point that is a compromise between the halfway point through the thin and thin wall thickness. Thicker tubing can often require higher laser power to cut fully through when a single pass process is being used. An alternative is to vary the linear speed of the laser cutter so that it is faster in the thinner regions and slower in the thicker ones. Prior to laser cutting the scaffold pattern the tube 40' may optionally be annealed at 10-20 degrees above the glass transition temperature of the tube polymer to work out residual stresses in the material resulting from the cutting process.

A second embodiment of a variable thickness scaffold is described next. In this description it is understood that use of the same element numbering for a scaffold described in connection with FIGS. 8A-8C carries with it the same meaning as in the prior discussion and the same description likewise applies for similar elements of the scaffold of FIGS. 6A-6C.

Figure 8A:
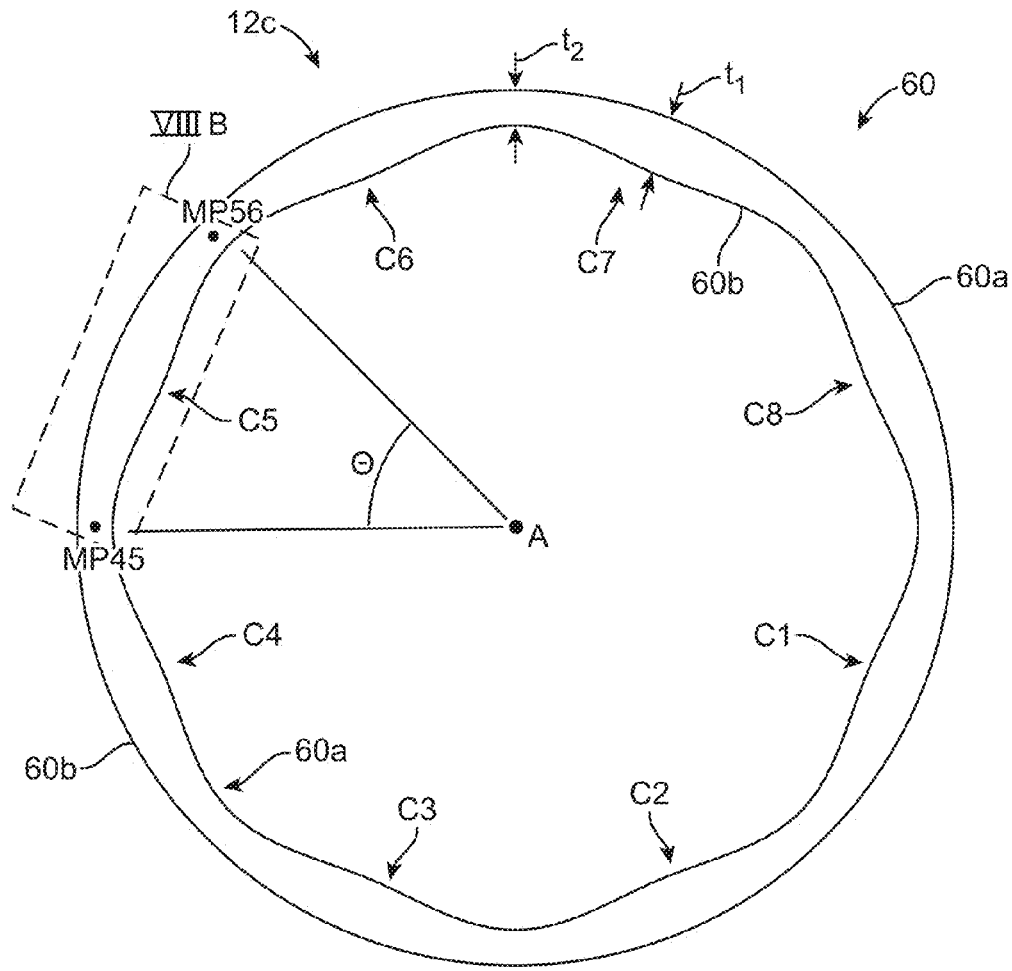
FIG. 8A is a cross-sectional view of a scaffold made from a variable wall thickness tube according to another embodiment. The scaffold has an undulating inner wall surface.

Referring to FIG. 8A there is shown a cross-sectional view of a scaffold according to a second embodiment. The scaffold 60 may have the same pattern of rings 12, crowns 14, struts 16, and links 18 as shown and described for scaffold 10. Similarly, the variance in wall thickness or undulating inner wall surface for the scaffold 60 may also be periodic over θ degrees between crowns, or the inner curved surface segment ("curved surface") repeats every 360/NC degrees where NC is the number of crowns in a ring. Thus, the inner curved surface repeats every θ=45 degrees for the illustrated 8 crown ring 12E and every θ=30 degrees for a 12 crown ring. As an example of the scaffold having 12, instead of the illustrated 8 crowns (FIG. 6B), and also considered part of this disclosure is the scaffold pattern described in US20100004735 at FIGS. 2, 4, 5A, 5B, 5C, 5D and paragraphs [0043]-[0062]. The inner curved surface repeats every θ=20 degrees for an 18 crown ring. As an example of a scaffold having 18 crowns and also considered part of this disclosure is the scaffold pattern described in US20110190872 at FIGS. 4, 5A, 6A, and paragraphs [0126]-[0130]. The variation in thickness for the scaffold 60 is between t1 and t2, where the ratio of t1 to t2, or t1/t2 is about 2.

The scaffold 60 differs from the scaffold 10 in that the inner wall surface 60b is undulating or wavy over the circumference, whereas scaffold 10 has a varying outer wall surface 10a. Additionally, the shape of the inner wall surface 60b varies differently from the shape of the outer wall surface 10a for the scaffold 10, as will now be described.

Figure 8B:
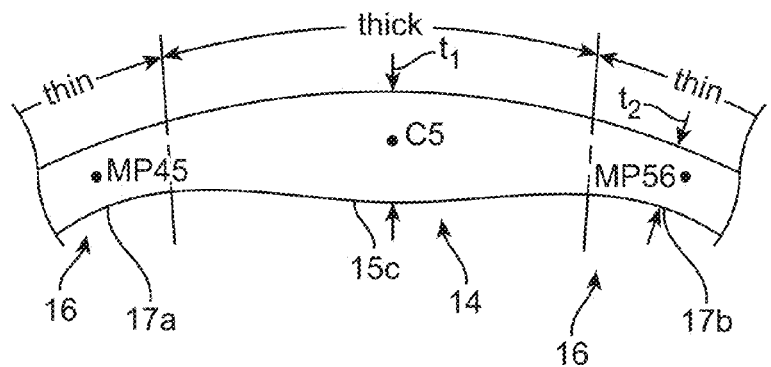
FIG. 8B shows in close-up a portion VIIIB of the scaffold in FIG. 8A.

Referring to FIG. 8B there is shown in close-up the portion VIIIB of the end ring 12e between midpoints MP45 and MP56 and showing crown C5. The curved surfaces described in FIG. 8B are the same as elsewhere over the inner wall surface for the scaffold 60. The portions designated as "thin" corresponds to a portion of the strut, e.g., about 60% to 90% of its length. Thickness variation from t2 over this portion of the strut length is 10% to 50% of t2, or the thickness t-thin satisfies the inequality t2<t-thin<1.5×t2. The thick part occupies the crown C5 and the remaining portion of the strut.

The outer surface extending between MP45 and MP56 may be described as follows. The surfaces 17a, 17b are rounded (or have no sharp corners) and are symmetric about the geometric center of the midpoints. Or the surfaces at the midpoints MP54, MP56 are rounded (or have no sharp corners) and symmetric about the respective midpoint.

The surface 15c extending between the surfaces 17a, 17b is concave, a continuously curved surface, and/or monotonically increasing from left to right or right to left in FIG. 8B from the surface 17a and 17b, respectively, to the crown center C5 that has the wall thickness t1. One example is a sinusoidal undulation periodic over the arc length between crown centers. The surface 15c according to other embodiments may be defined by a radius of curvature, i.e., the concave shape follows the arc of a circle centered equidistant between the midpoints MP45, MP56, with ends of the surface 15c being continuous with surfaces 17a, 17b to avoid sharp edges that can lead to stress concentrations during loading. One difference between the thickness variation shown for the scaffold 60 and scaffold 10 is that in scaffold 60 the struts are made thicker nearer to the crowns. Surface 17a, 17b, 15c may be sinusoidal. Alternatively, the surface may include parabolic shapes centered about the midpoints MP45, MP56 and extending to near to, or to a crown on each side of the respective midpoints. The surface may alternatively include hyperbolic shapes extending between the midpoint MP45 and crown C4 and the midpoint MP56 and the crown C5. And the curvature at the midpoints MP45, MP56 may be the same as, less than or greater than the curvature at the crown C5. Examples of embodiments of inner curved surfaces according to other embodiments are shown and described in connection with FIGS. 6D, 6E and 6F.

Referring again to FIG. 8A, each of the link elements 18 extending between the rings 12 have the same thickness t1 as at the crowns for the scaffold 60. In one particular embodiment the thickness t1 is chosen to improve the retention of a radiopaque marker in a link element. Such a link element is illustrated in FIG. 6A as link 30, which has holes formed in it to hold radiopaque markers 32. For embodiments having a thickness t1 to improve retention of the marker 32 in the hole the thickness is between 120 and 150 microns, about 125 microns, or up to 160 microns. According to another embodiment of a scaffold for increasing retention of a marker, a tube is made to have only one, or two thick parts. These thick parts correspond to links where the markers will be held in the scaffold cut from the tube. For example, the thick parts corresponding to one or both of crowns C2 and C6. Alternatively, the tube is made to have only two thick parts separated by 180 degrees. According to these embodiments the scaffold has a wall thickness of about 80 to 100 microns everywhere, except for the region between strut midpoints surrounding links where a marker will be held on the scaffold. There a wall thickness of at least 120 microns is made.

In alternative embodiments a scaffold may have the repeating curved surface illustrated in either FIG. 6C or FIG. 8B and the accompanying description, and the undulating surface may be found at either the inner wall or the outer wall. When it is desirable to make an undulating surface on the outer wall the method described above in connection with FIGS. 7A-7C and FIG. 11 may be used to make this surface. When it is desirable to make an undulating surface on the inner wall one of the methods described in connection with FIG. 9 or 10, below, may be used.

Figure 8C:
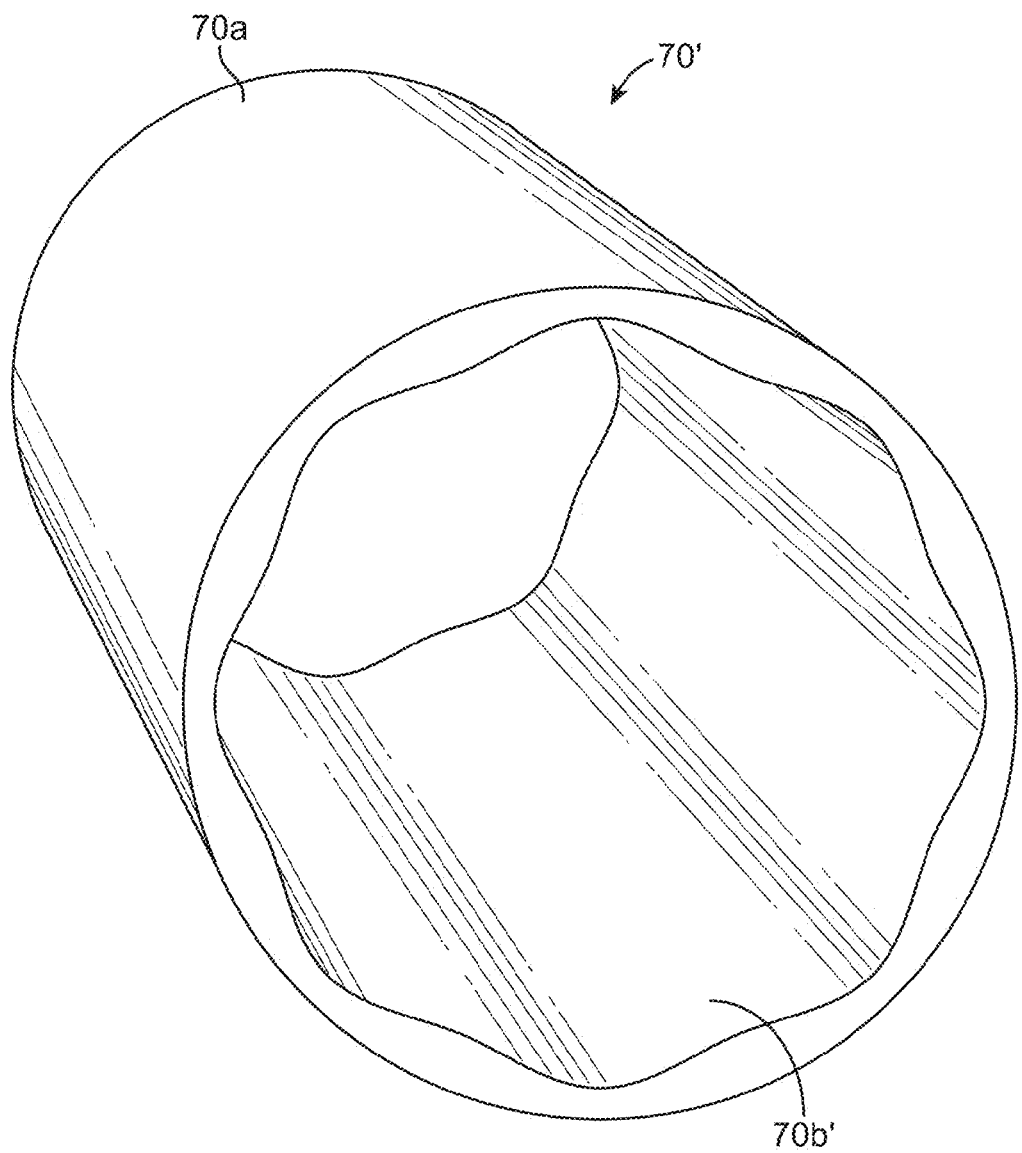
FIG. 8C is a perspective view of a tube used to make the scaffold of FIG. 8A.

Referring to FIG. 8C there is shown a perspective view of a tube 70' made to have a contoured inner wall surface 70'b for the scaffold 60 (FIG. 8A) and outer wall surface 70a that describes a cylinder. The tube 70' may be made according to either of the processes described below.

Figure 9:
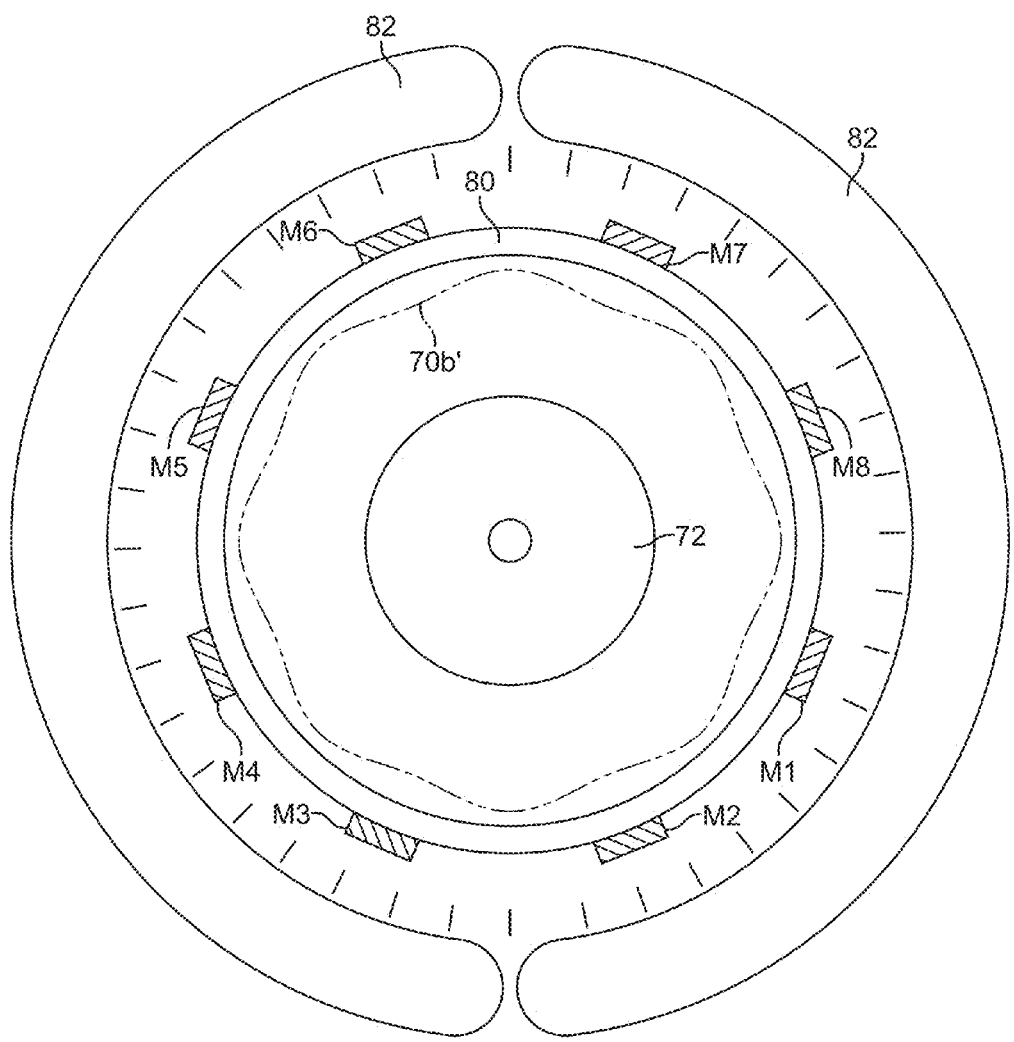
FIG. 9 is a schematic illustration of a first method for making the tube of FIG. 8A.

Referring to FIG. 9 there is shown schematically a blow-molding process configured to make the tube 70' with the contoured inner wall surface 70b' (shown in phantom) and cylindrical outer surface. A precursor tube 72, while being heated by light bulbs 82 (UV lights), is radially expanded lengthwise at a given processing rate (along the longitudinal axis) and expansion pressure/rate within a glass mold 80 while the tube 72 is under axial tension. Expansion occurs at an axial position near the moving light bulbs. Examples of processes that may be used to perform a biaxial expansion in this manner are described in US20110066222 at FIGS. 3A, 3B, 3C, 3D and paragraphs [0047] through [0062]. Processing parameters, e.g., heating temperature, translation rate, pressure, draw ratio radially and axially, that may be used for blow molding are described in paragraphs [0077] through [0097]. These aspects of the blow-molding process described in US20110066222 is modified in the following way to produce the contoured inner surface 70b'.

A cylindrical mask (illustrated schematically by mask elements M1-M7) is interposed between the lamps 82 and the glass mold 80. The mask may contain a series of longitudinal slits, holes to vary the light transfer in a circumferential manner. The mask could be made of metal. Or the mask could be made of a transparent material and be tinted, colored or painted in a circumferentially varying manner.

The mask elements M1-M7 blocking all or a portion of the light energy emitted from the lamps 82 are located on the exterior of the glass tube 80 at circumferential locations registered with the locations of thick parts 101 (FIG. 7A) or the locations of the crowns 14 links 18 that will be later cut from the biaxially expanded tube. For a scaffold having crowns C1, C2, C3, C4, C5, C6, C7 and C8 per ring there may be eight respective light blocking or filtering mask elements M1, M2, M3, M4, M5, M6, M7 and M8 that are configured to diffuse, reflect or filter light energy. The masks create local thick spots due to the lower temperature of these parts of the tube during biaxial expansion. The hotter portions that receive a greater amount of the light energy create local thin spots. By varying the temperature in this way during the biaxial expansion one may produce the wavy or undulating surface 70b' for the expanded tube 70'.

TABLE 1 provides processing parameters and mask characteristics for making a scaffold according to FIGS. 8A and 9, where the tube has a 400%-500% radial draw, the tube material is PLA or a blend of PLA and PCL, and the wall thickness varies between t1=130 microns and t2=80 microns.

TABLE 1

| | |
|---|---|
| Average temperature | 50-120 Deg. C. |
| Temperature difference (hot and cold spots) | 5-50 Deg. C. |
| Pressure | 100-125 psi |
| Bulb translation rate | 0.2-0.5 mm/sec |
| Mask properties | 0% to 50% transmittance |

Figure 10:
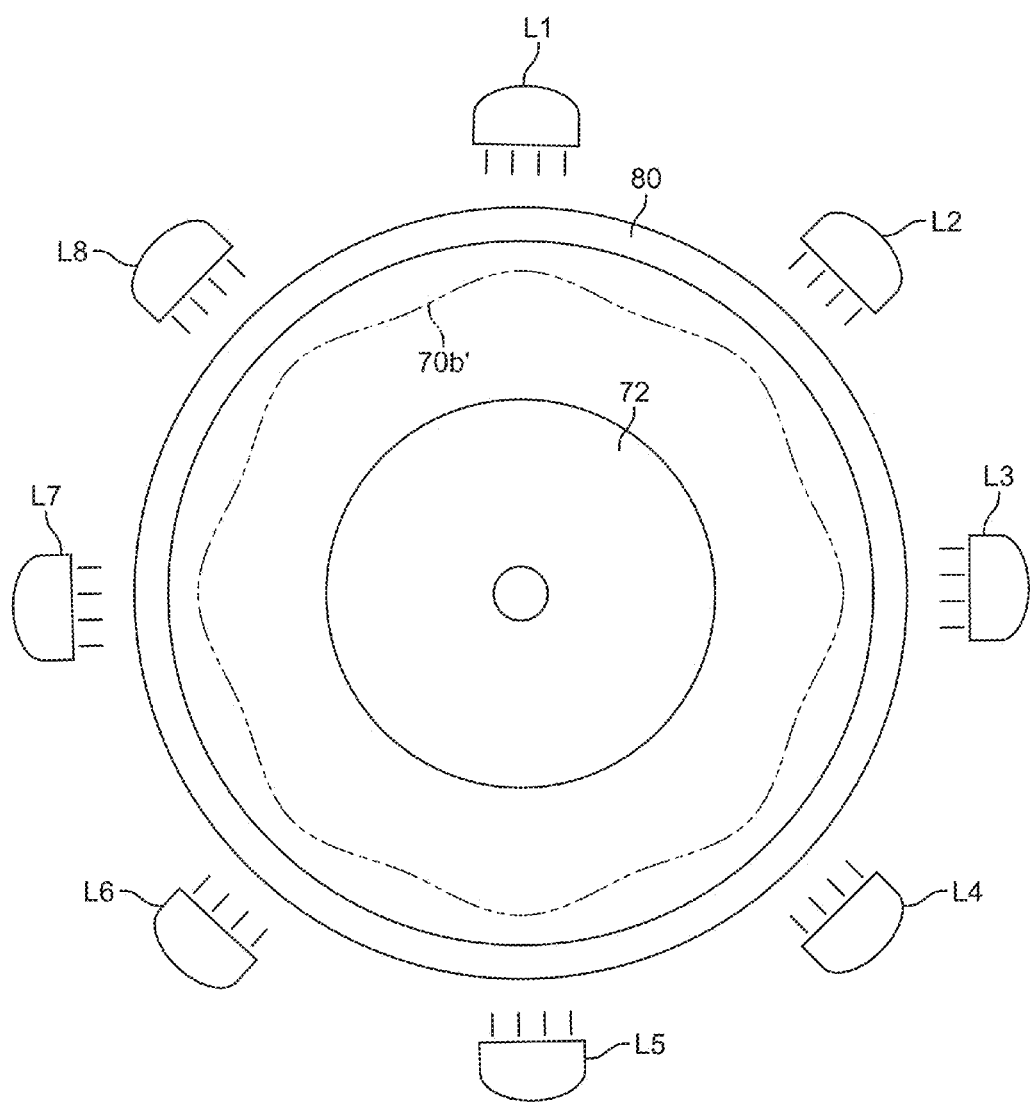
FIG. 10 is a schematic illustration of a second method for making the tube of FIG. 8A.

Referring to FIG. 10 there is shown schematically an alternative method for producing a variable wall thickness tube during a biaxial expansion of the precursor tube 72. Rather than disposing a mask between a uniform light source and the glass mold 80, individual lighting elements L1, L2, L3, L4, L5, L6, L7, and L8 are placed over the respective thin sections 102 or midpoints MPnm (n, m=1 . . . 8) where struts will be cut from the tube 70'. Thus, in this embodiment local heat sources are applied strategically to introduce controlled thin spots around the tubing circumference. Multiple light, or heat sources, are used. The number and spacing are chosen to produce the desired periodicity of thin regions between crowns for the scaffold pattern. For example, if there are 8 crowns per ring there are 8 lights translated, each of which positioned between crowns.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A medical device, comprising: a tubular body made from a polymer material, the tubular body having one of an undulating inner wall surface and an undulating outer wall surface such that a ratio of a maximum wall thickness (t-max) to a minimum wall thickness (t-min) for the tubular body is between 2 and 1.2;
   wherein the one of an undulating inner wall surface and an undulating outer wall surface comprises a curved surface that repeats every 20, 30, or 45 degrees about a circumference of the tubular body;
   wherein the tubular body is a scaffold having interconnected elements comprising a first ring connected to a second ring by a link; and
   wherein the first ring and the second ring have crowns interconnected by struts.

2. The medical device of claim 1,
   wherein for the curved surface that repeats every 20 degrees the first and second rings have 18 crowns, wherein for the curved surface that repeats every 30 degrees the first and second rings have 12 crowns, and wherein for the curved surface that repeats every 45 degrees the first and second rings have 8 crowns.

3. The medical device of claim 1, wherein the curved surface is described by one period of a sinusoid, a portion of the curved surface is parabolic, or a portion of the curved surface is hyperbolic.

4. The medical device of claim 1, wherein the curved surface is concave between crowns.

5. The medical device of claim 1, wherein the curved surface is convex between struts.

6. The medical device of claim 1, wherein the curved surface comprises a first curvature centered over a crown and a second curvature centered over a midpoint between crowns, and wherein the first curvature is less than the second curvature.

7. The medical device of claim 1, wherein the curved surface comprises a first curvature centered over a crown and a second curvature centered over a midpoint between crowns, and wherein the first curvature is greater than the second curvature.

8. The medical device of claim 1, wherein the wall thickness is t-max at the crowns and the wall thickness monotonically decreases from t-max to t-min, wherein a strut midpoint has a wall thickness of t-min.

9. The medical device of claim 1, wherein the link is arranged parallel to a longitudinal axis of the scaffold and has a wall thickness t-max, and a width less than a strut width to reduce occurrence of backflow downstream of a crown when the scaffold is implanted within a vessel and to reduce a crimped diameter for the scaffold.

10. The medical device of claim 1, wherein the crowns and the link have a wall thickness of t-max and the struts have a wall thickness of t-min.

11. The medical device of claim 1, wherein t-max and t-min are one of:
   250 and 150 microns, respectively;
   100 microns and 75 microns, respectively;
   130 microns and 90 microns, respectively; or
   150 microns and 100 microns respectively.

12. The medical device of claim 1, wherein t-max is between 160 and 130 microns or 130 and 100 microns.

13. The medical device of claim 1, wherein t-min is between 100 and 75 microns or 90 and 70 microns.

14. The medical device of claim 1, wherein the other of the outer wall surface and the inner wall surface describes a cylinder.

15. The medical device of claim 1, wherein the medical device comprises a composition including poly(l-lactide).

16. The medical device of claim 1, wherein the tubular body is a biaxial expanded tubular body.

17. The medical device of claim 1, wherein both the inner and outer wall surfaces are undulating.

18. A medical device, comprising: a scaffold made from a polymer material and having interconnected elements, the scaffold made from a polymer material and having interconnected elements, the scaffold having one of an undulating inner wall surface and an undulating outer wall surface such that a ratio of a maximum wall thickness (t-max) to a minimum wall thickness (t-min) for the scaffold is between 2 and 1.2;
  wherein the one of an undulating inner wall surface and an undulating outer wall surface comprises a curved surface that repeats every 180 degrees about a circumference of the scaffold;
  the interconnected elements comprising:
  a first ring connected to a second ring by a first link and a second link,
  the second ring connected to a third ring by a third link and a fourth link,
  the first link and the second link are separated by 180 degrees and each hold a radiopaque marker, and the first link and the second link have the wall thickness t-max, and the third link and the fourth link have the wall thickness t-min.

19. A medical device, comprising:
  a tubular body made from a polymer material, the tubular body having one of an undulating inner wall surface and an undulating outer wall surface such that a ratio of a maximum wall thickness (t-max) to a minimum wall thickness (t-min) for the tubular body is between 2 and 1.2;
  wherein the tubular body is a scaffold, comprising:
    a first ring, a second ring and a third ring, each of the rings having a number of crowns (NC) interconnected by struts,
    each of the struts of the first ring, second ring and third ring comprise the t-min wall thickness,
    each of the crowns of the first ring, second ring and third ring comprise the t-max wall thickness, and
    when viewed in cross section the one of an undulating inner wall surface and an undulating outer wall surface repeats every 360/NC degrees about a circumference of the scaffold.

20. The medical device of claim 19, wherein the scaffold has 18 crowns (NC=18) whereby the one of an undulating inner wall surface and an undulating outer wall surface repeats every 20 degrees.

* * * * *